(12) United States Patent
Livne et al.

(10) Patent No.: US 8,070,688 B2
(45) Date of Patent: Dec. 6, 2011

(54) DEVICE AND METHOD FOR PUPIL SIZE MODULATION

(75) Inventors: Abraham Livne, Kfar Saba (IL); Ilan Ron, Kfar Saba (IL)

(73) Assignee: A.T.I.-Advanced Medical Technologies Ltd., Hod Hasharon (IL)

( * ) Notice: Subject to any disclaimer, the term of this patent is extended or adjusted under 35 U.S.C. 154(b) by 571 days.

(21) Appl. No.: 11/909,103

(22) PCT Filed: Mar. 21, 2006

(86) PCT No.: PCT/IL2006/000362
§ 371 (c)(1),
(2), (4) Date: Sep. 19, 2007

(87) PCT Pub. No.: WO2006/100677
PCT Pub. Date: Sep. 28, 2006

(65) Prior Publication Data
US 2008/0161716 A1    Jul. 3, 2008

(30) Foreign Application Priority Data

Mar. 21, 2005  (IL) .......................................... 167559

(51) Int. Cl.
*A61B 13/00* (2006.01)
*A61B 5/103* (2006.01)
*A61B 5/117* (2006.01)
*A61B 3/00* (2006.01)
*A61N 1/00* (2006.01)

(52) U.S. Cl. ............ 600/558; 600/587; 607/53; 607/54; 351/200

(58) Field of Classification Search ................. 600/372, 600/373, 382, 383, 544–548, 554, 558, 587, 600/595; 607/1, 2, 53, 54; 351/200
See application file for complete search history.

(56) References Cited

U.S. PATENT DOCUMENTS

| 5,522,864 A | 6/1996 | Wallace et al. |
| 6,101,411 A | 8/2000 | Newsome |
| 6,291,498 B1 | 9/2001 | Horn |
| 6,420,407 B1 | 7/2002 | Horn |
| 6,515,006 B2 | 2/2003 | Horn |
| 6,730,065 B1 | 5/2004 | Horn |

FOREIGN PATENT DOCUMENTS

| JP | 62-268572 | 11/1987 |
| JP | 10-192421 | 7/1998 |
| WO | 98/51292 A1 | 11/1998 |
| WO | 02/11648 A1 | 2/2002 |
| WO | 02/085245 A2 | 10/2002 |

OTHER PUBLICATIONS

European Search Report dated Nov. 10, 2010 from corresponding EPC Appn. No. 06711339.9, published Dec. 19, 2007, 2 pgs.

*Primary Examiner* — Jeffrey G Hoekstra
(74) *Attorney, Agent, or Firm* — Frommer Lawrence & Haug LLP; William S. Frommer

(57) ABSTRACT

A device and method are presented for drug-free, non-invasive, modulation of a size of a patient's pupil. The invention utilizes application of an external electric and/or magnetic field of desired properties to the patient's iris to thereby effect stimulation or neutralization of synapses and thus temporarily inducing mydriasis or miosis effect.

26 Claims, 10 Drawing Sheets

DEVICE AND METHOD FOR PUPIL SIZE MODULATION

FIELD OF THE INVENTION

This invention is generally in the field of medical devices and relates to a device and method for pupil size modulation (dilation or contraction).

BACKGROUND OF THE INVENTION

Every person, irrespective of whether he is healthy or not, has to at least once undergo an eye examination/treatment that requires pupil dilation. Those having various eye problems (e.g., macular degeneration, diabetes, etc.) require repeated pupil-dilated eye examinations. The pupil dilation (mydriasis) is typically induced by application of a dilator drug (typically atropine) to the patient's eye followed by waiting several minutes before the pupil is sufficiently dilated to enable the eye examination.

Various types of a dilator drug, known as mydriatic agents, have been developed. For example, WO 98/51292 discloses pharmaceutical compositions which include a therapeutically effective amount of a stereoscopically-pure enantiomer, preferably (+)-phenylephrine is substantially free of (−)-phenylephrine.

Furthermore, the conventional pupil dilation procedure results in a recovery period of a few hours, whilst the patient suffers from excessive light reaching the retina accompanied by focusing difficulties. Moreover in this recovery period, it is highly recommended that the patient will refrain from driving or doing dangerous tasks.

Constriction of a pupil size (miosis) is required for individuals suffering from excessive pupillary dilation, e.g., in dim light or through medication. Various drug-based treatments suitable to be used for this purpose are disclosed for example in the following patents: U.S. Pat. Nos. 6,730,065; 6,515,006; 6,420,407; 6,291,498.

It is known to use the principles of electrophoresis to assist the drug delivery process (e.g., deliver of vitamins, such as Vitamin C). Electrophoresis is an electrochemical process in which colloidal particles or molecules with a net electric charge migrate in a solution under the influence of an electric current. This process is also termed "iontophoresis" or "cataphoresis".

U.S. Pat. No. 6,101,411 discloses a dilation enhancer apparatus, which is a hand held electrophoretic device using a contact lens type delivery system to provide rapid clinically useful dilation of the pupil of the eye. The apparatus includes a contact lens with a conductive outer shell (one electrode of a two-electrode electrophoresis device) and a preferably soft, preferably disposable contact lens for contacting a patient's eye that assists in delivering dilation drops or other medicaments to a patient's eye. Advantageously, the lens is used with a relatively small hand-held power source. Electrophoresis can be used to help deliver dilation drops more rapidly, regardless of the delivery apparatus used for the electrophoresis.

SUMMARY OF THE INVENTION

There is a need in the art to facilitate the pupil dilation/constriction process by providing a novel device and method for quickly and effectively inducing a temporarily pupil dilation (mydriasis) or contraction (miosis) without a need for eye drops, and with rapid recovery.

The present invention is based on the understanding of the effects of neuron electrical signals propagation at the synapse, or any other part of the nervous system, associated with the pupil control muscles. Electrical signals are propagated through the synaptic cleft, using neurotransmitters. A Neurotransmitter is a substance synthesized in neurons (nerve cells) and released across the synaptic cleft (a space between neurons) in response to an action potential. A Neurotransmitter or the so-called "chemical messenger" thus presents a chemical signal carrying an electrical impulse passing through a human body.

The technique of the present invention provides for controllably affecting the action potential (to which the neurotransmitter is responsive) by applying an external electric and/or magnetic field, aimed at either neutralizing or enhancing this action potential. Alternatively, the technique of the present invention provides for controllably inhibiting neurotransmitters from reaching their destination (receptors) by applying an external electric and/or magnetic field in opposite or diverting directions other than the neurotransmitters path.

The most important function of the iris is to control the pupil size. The iris muscles regulate the pupil size and thus control the amount of light that can enter the pupil and fall on the retina. The pupil size is controlled by two sets of internal iris muscles: radial (dilator) muscles that allow pupil expansion, and circular muscles that allow pupil contraction.

The technique of the present invention provides for controllably stimulating or paralyzing the respective muscles of iris by either neutralizing or stimulating their related synapses connections. Mydriasis can be reached by either paralyzing the circular muscles and/or stimulating the radial muscles, and miosis—vice versa. When both the circular and radial muscles are paralyzed or do not receive any stimulus, the basic tonus of the dilator (radial) muscles overcomes the tonus of the circular muscles, and the pupil is dilated, thus Mydriasis can also be obtained.

Alternatively, the technique of the present invention provides for obtaining the Mydriasis effect by differentially applying an electric field to affect the contractor muscles more than the dilator muscles. The differential effect can be achieved by applying the field in a direction, which is perpendicular to the contractor muscles and parallel to the dilator muscles, so that the field would inhibit the action potential, and/or movement of charged particles, in the contractor muscle more than in the dilator muscle. Alternatively, since the dilator muscles are more interior to the contractor muscles, the electric field would pass through the human tissue before reaching the dilator muscles, and would thus be attenuated significantly. This reduces its effect on the dilator muscles, so that it is smaller than the effect on the contractor muscles.

The present invention thus provides a drug-free, non-invasive modulation of a pupil size (dilation/contraction of the pupil), by temporarily inducing the mydriasis or miosis effect, by means of subjecting the iris to an external electric and/or magnetic field of desired properties (direction and intensity). The field effects stimulation or neutralization of the iris muscles synapses.

According to one embodiment of the invention, depolarization is applied to the iris through an electric field of negative polarity. This may cause the synapses stimulation by enhancing the action potential. According to another embodiment, repolarization is applied through an electric field of positive polarity, thus achieving synapses neutralization by reducing the action potential. According to yet another embodiment of the invention, an external field is applied so as to deflect or divert the neurotransmitters from their original direction of propagation, thus inhibiting neurotransmitters to pass through the synapses and preventing them from reaching their respective receptors. Hence, the synapses neutralization can be achieved by applying an electric field in either opposite or substantially orthogonal direction to the neurotransmitters original direction of propagation in the body.

The resulting recovery time is measured in seconds, thus eliminating or at least substantially reducing the associated lingering side-effects of commonly used Mydriasis inducing methods.

According to yet another embodiment of the invention, the iris is subjected to an external magnetic field directed substantially perpendicular to the neurotransmitters path, using the principles of the known Van Allen radiation belts' effect. In the Van Allen belts, charged particles are trapped in the Earth's magnetic field. A force on the charged particles is normal to the magnetic field lines. These highly energetic charged particles actually move in helical paths around the magnetic field lines. As the charged particles move closer to the earth's magnetic poles, the force increases until the particle can no longer move any farther forward and gets repelled back down to repeat the process with the opposite pole.

The present invention provides for any drug free, non-invasive, temporary neutralization or stimulation of neuron electrical signals at the synapse, or any other part of the nervous system, associated with the pupil control muscles. Such effects include, but are not limited to, local anesthetic, tension relief, etc.

Thus, according to one broad aspect of the present invention, there is provided a device for modulation of a pupil size, the device comprising a source of electric and/or magnetic field configured and operable for creating said field(s) of desired properties in a region of a patient's eye to thereby effect stimulation or neutralization of synapses or any other part of the nervous system, associated with the pupil control muscles, and thus temporarily induce mydriasis or miosis effect, the device thereby providing a drug-free modulation of a pupil size.

The device may be of a simple configuration including only a source of the external electric and/or magnetic field. The field source is configured and operable to define a field region where the patient's eye is to be located and create the external field of required intensity and direction in the field region.

The device may also include a field sensor and a control unit. The sensor is located in the vicinity of the field region and is configured for measuring the actual field intensity and generating feedback data indicative thereof. The control unit is configured to be responsive to required field intensity settings and the feedback data indicative of the measured field intensity for processing and analyzing this data, and upon detecting that adjustment of the field intensity is required, generating a respective control signal to the field source unit. Alternatively the operator can adjust the voltage and/or current level(s) according to noticeable effect, thus dismiss the use of the sensor and the associated control loop.

The external electric field source includes a voltage supply unit, and defines an electrode arrangement, a potential difference between the electrodes defining a field region. Such an electrode arrangement may be defined by one of the following options: the device may include at least one pair of electrodes, one being an "ocular" electrode and the other being a "complementary" electrode; or the device may include only the ocular electrode while the complementary end of the circuit is constituted by direct contact to patients body. The electric field between the electrodes is thus of a substantially constant profile.

The first electrode, termed "Ocular electrode", is preferably configured to be brought close to the patient's eye, and has an electrically insulated surface by which it is brought to the proximity of the patient's eye. The second electrode, termed "Complementary electrode", is configured to be situated in a position to facilitate for an electric field region where the patient's eye is to be located. This electrode may be attached either to the patient's head or to a seat headrest, or any other means of mounting it in the required position, or may be constituted by direct contact to the patient's body. The second, complementary electrode may be carried by a head band to be put on the patient's head. The field sensor may be attached to this head band.

If the application of the external magnetic field is considered, the magnetic field source includes an electro-magnet unit (such as a coil unit or superconductor arrangement) serving as an ocular element; and a power (current) supply unit.

The ocular element (electrode or electro-magnet unit) preferably has an annular shape to enable inspection of the eye via a hole of the ocular element. The annular-shaped ocular element is preferably configured for mounting a lens in the electrode hole.

The device may be designed as a hand held probe, or as a probe for mounting it on the slit lamp table. Such a probe device contains the voltage/current supply unit (and possibly also the control unit), where the ocular element (electrode or electro-magnet unit) is located outside the probe housing and is connected to the voltage/current supply unit by an electrically insulated connector. Preferably, a display may be located at the outer surface of the housing to be exposed to the user. Also, the complementary electrode can reside on the held hand device.

According to another broad aspect of the present invention, there is provided a device for use in dilation/contraction of a patient's pupil, the device comprising: a source of an external electric and/or magnetic field configured and operable to define a field region where the patient's eye is to be located and create the external field of required properties in said field region to thereby temporarily induce an effect of mydriasis or miosis; a sensor located in the vicinity of said field region and configured for measuring the actual field intensity and generating data indicative thereof; and a control unit configured to be responsive to the data indicative of the measured field intensity to process and analyze said data and upon detecting that adjustment of the field value is required generate a feedback signal to a voltage supply unit of the field source.

According to yet another aspect of the invention, there is provided a device for use in dilation/contraction of a patient's pupil, the device comprising: a housing containing a voltage supply unit operable to supply voltage to an electrode located outside said housing and connected to the voltage supply unit via a connector extending from the housing to said electrode, the electrode having a substantially annular shape so as to enable, when brought close to a patient's eye, visual observation of the eye via an opening defined by the annular-shaped electrode.

According to yet another broad aspect of the invention, there is provided a device for use in dilation/contraction of a patient's pupil, the device comprising: a housing containing a current supply unit operable to apply current to an electro-magnet unit located outside said housing and connected to the current supply unit via a connector extending from the housing to said electro-magnet unit, the electro-magnet unit having a substantially annular shape so as to enable, when brought close to a patient's eye, visual observation of the eye via an opening defined by the annular-shaped electro-magnet unit.

The housing may be configured to be held by user, or to be mounted on a slit lamp table.

According to yet another broad aspect of the invention, there is provided a method for drug-free modulation of the size of a patient's pupil, by applying an external electric and/or magnetic field of desired properties to the patient's iris to thereby effect stimulation or neutralization of synapses and thus temporarily inducing mydriasis or the miosis effect.

According to yet another aspect of the invention, there is provided a method for a drug free, non-invasive, temporary neutralization or stimulation of neuron electrical signals at the synapse, or any other part of the nervous system, associated with the pupil control muscles in a region of interest of a human body, the method comprising applying an external electric and/or magnetic fields to the region of interest.

BRIEF DESCRIPTION OF THE DRAWINGS

In order to understand the invention and to see how it may be carried out in practice, preferred embodiments will now be described, by way of non-limiting examples only, with reference to the accompanying drawings, in which.

DETAILED DESCRIPTION OF THE INVENTION

The present invention provides for a drug-free modulation of a pupil size (dilation/contraction of the pupil), by effecting stimulation or neutralization of the synapses by subjecting the patient's iris to an external electric and/or magnetic field of desired properties (direction and intensity).

Figure 1A:
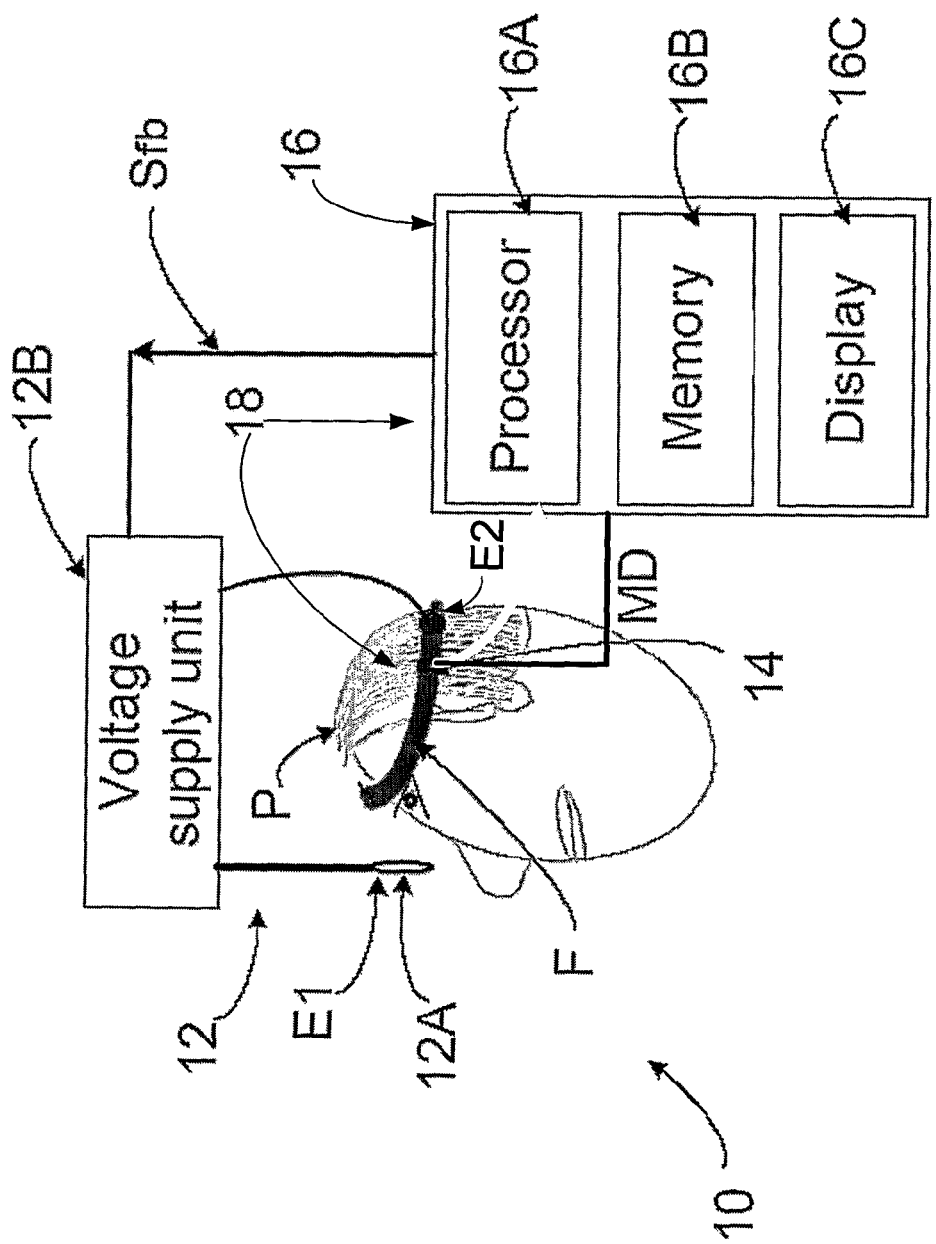
FIGS. 1A and 1B are schematic illustrations of an example of a device of the present invention for appropriately modulating the pupil size, utilizing an electric field source.
Figure 1B:
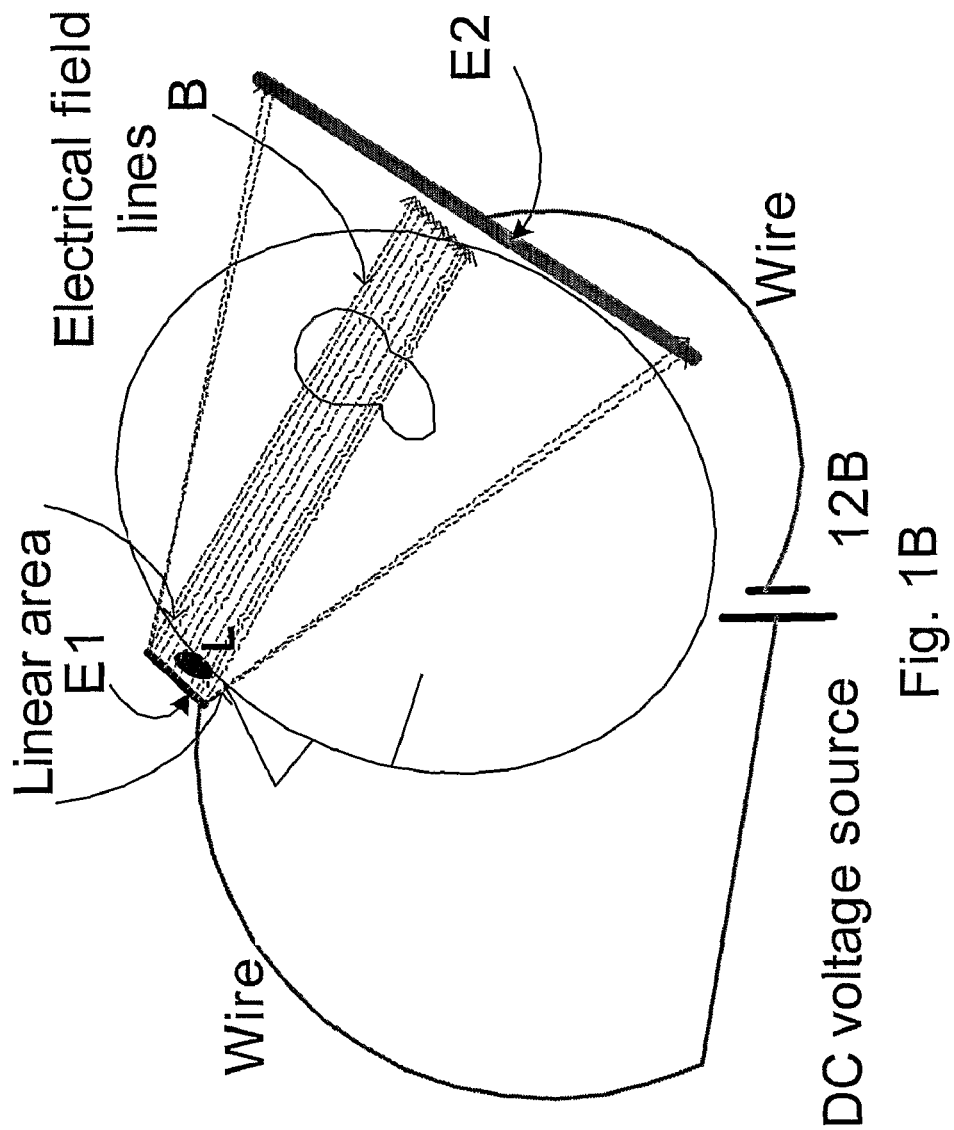

Referring to FIGS. 1A and 1B, there is schematically illustrated an example of a device 10 of the present invention for use in modulating (dilating/contracting) the pupil size of a patient P. The device 10 includes a source 12 of an external electric and/or magnetic field, associated with a power source (preferably a battery pack or adapter input plug) which is not specifically shown here.

Field source 12 is configured and operable to create a DC electric field of a required profile within a field region FR. The field profile defines a required field value within a patient's eye (iris) location L in the field region. By this, an effect of mydriasis or miosis of the iris (depending of the field value) is temporary induced, namely during the application of said field.

In the present example, an electric field is considered. Electric field lines B are shown in FIG. 1B. The electric field source 12 includes an electrode arrangement 12A and a voltage supply unit 12B.

The electrode arrangement 12A of the device 10 includes two electrodes $E_1$ and $E_2$ kept at a required potential difference between them. The electrodes are accommodated in a spaced-apart relationship to be at opposite sides of the patient's head such that the field lines B mostly pass through the iris location L. One electrode $E_1$ is preferably configured to be brought close to the patient's eye and is termed "ocular element" or "ocular electrode", and the other electrode $E_2$, termed "complementary electrode", may be either attached to a patient's chair (seat head rest) so as to be close to the patient's head or carried by a band F to be put onto the patient's head (as shown in FIG. 1A).

It should be noted, that according to the invention the ocular electrode $E_1$ is fully insulated, in order to prevent electrocution hazard. The complementary electrode $E_2$ may also be completely insulated or may be grounded. The complementary electrode presents a complementary part of the electric field lines, to ensure that some field lines pass through the pupil area. If the use of a conductive insulated element in a complementary electrode is considered, such an element may be attached to the patient's body, and the patient's body thus becomes the complementary electrode. The electric potential is thus equalized in the body. It should be understood that no electric current flows between the electrodes, since the ocular electrode is still fully insulated. In a similar manner, both the complementary electrode and the patient's body may have a conductive path to the ground.

The ocular electrode $E_1$ is preferably of an annular shape defining a hole large enough to enable visual inspection of the eye via the enlarged pupil. The ocular electrode hole may be used for combining lenses commonly used by eye physicians for retina examination, such as slit lamp using 78D and 90D lenses; or indirect opthalmoscope using a 20D lens.

The electric field profile within the field region FR and accordingly the field intensity at the iris location L within this region is defined mainly by a potential difference between the electrodes $E_1$ and $E_2$ and a distance between the electrodes. The electric field between two electrodes inhibits nervous impulses to iris muscles. It should be noted that the voltage polarity can be of either type.

In order to desirably affect the pupil size (e.g., achieve a mydriasis effect), a minimal field intensity level should be created at the iris location L. This field intensity depends mainly on the following factors: the applied voltage, distance and attitude of each electrode with respect to the iris, and dielectric characteristics of the specific patient.

Preferably, the device 10 utilizes a closed-loop control circuit 18. The latter is formed by a field sensor 14 located within the field region FR and configured and operable for measuring the actual field intensity value and generating data indicative thereof; a control unit 16 connectable to field source 12 and field sensor 14, and the voltage supply unit 12B. Thus, the required field intensity at location L is set by user (operator) and controlled using a feedback signal of the control unit 16 based on data measured by the field sensor 14. Alternatively, the operator can adjust the voltage level according to noticeable effect, thus eliminating the need for the control loop (sensor and control unit).

The device of the present invention thus provides for affecting synaptic transmission to desirably modulate the pupil size. This is implemented either by contradicting the natural action potential by applying the parallel field; or by inhibiting neurotransmitters arrival to receptors by diverting them from their course using an orthogonal field, as will be described below.

The electric field sensor 14 may have any known suitable configuration, for example a flux meter, an electro-optic detector for example of the type based on an optical Fabry-Perot sensing cavity. The voltage supply unit 12B is a high voltage DC circuit generating the required potential difference (e.g., about 80-200V) between the electrodes.

The control unit 16 is typically a computer system, including inter alia a memory utility 16A for storing certain reference data (e.g., calibration data), a processor 16B, user interface utility 16C (e.g., display). The control unit 16 operates for maintaining the required field intensity (in response to the data coming from the field sensor 14) and supervising the device. The control unit 16 receives measured data MD indicative of the measured field value, processes and analyzes this data and operates the field source (voltage supply unit 12B) accordingly when adjustment of the field source operation is required to provide the desired field intensity value in the region of interest. To this end, the control unit 16 is appropriately preprogrammed to set the field value level either in a digital format or as an explicit voltage level, and to generate a field intensity control signal $S_{fi}$ to operate the voltage supply unit 12B. The control unit 16 may display the set value and the device status.

Figure 2A:
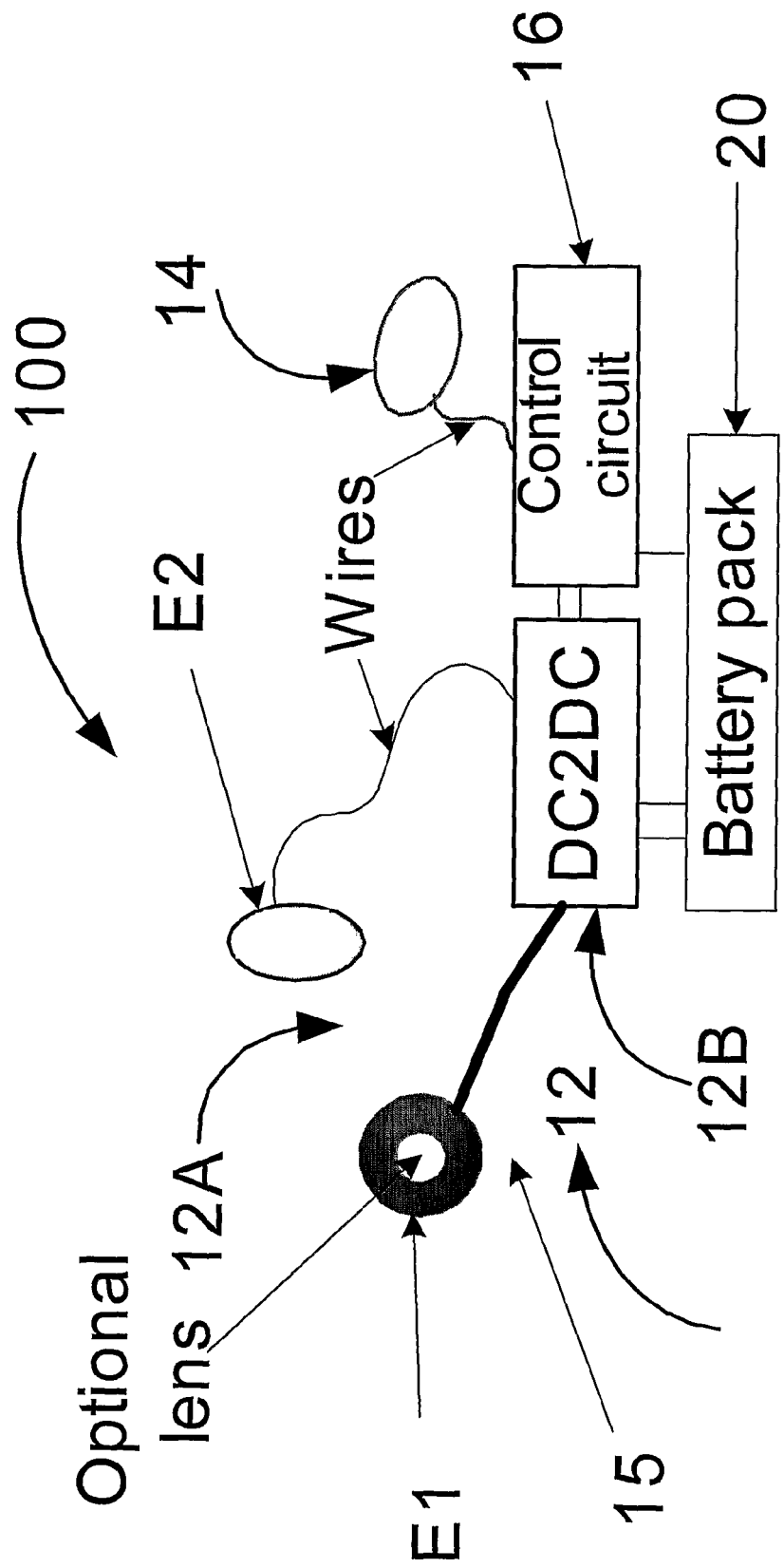
FIGS. 2A to 2C exemplify the specific implementation of the device of FIGS. 1A-1B.
Figure 2B:
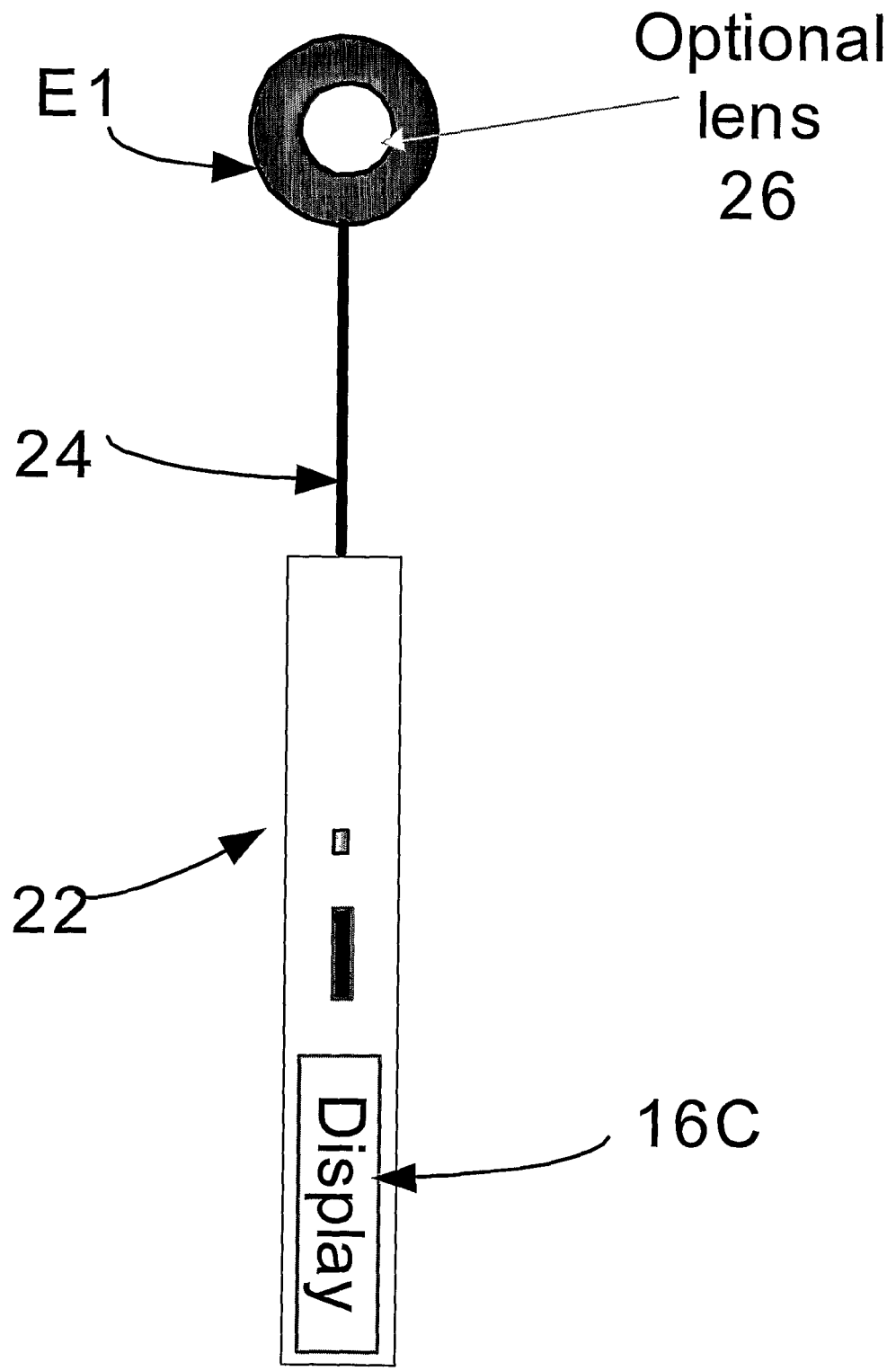
Figure 2C:
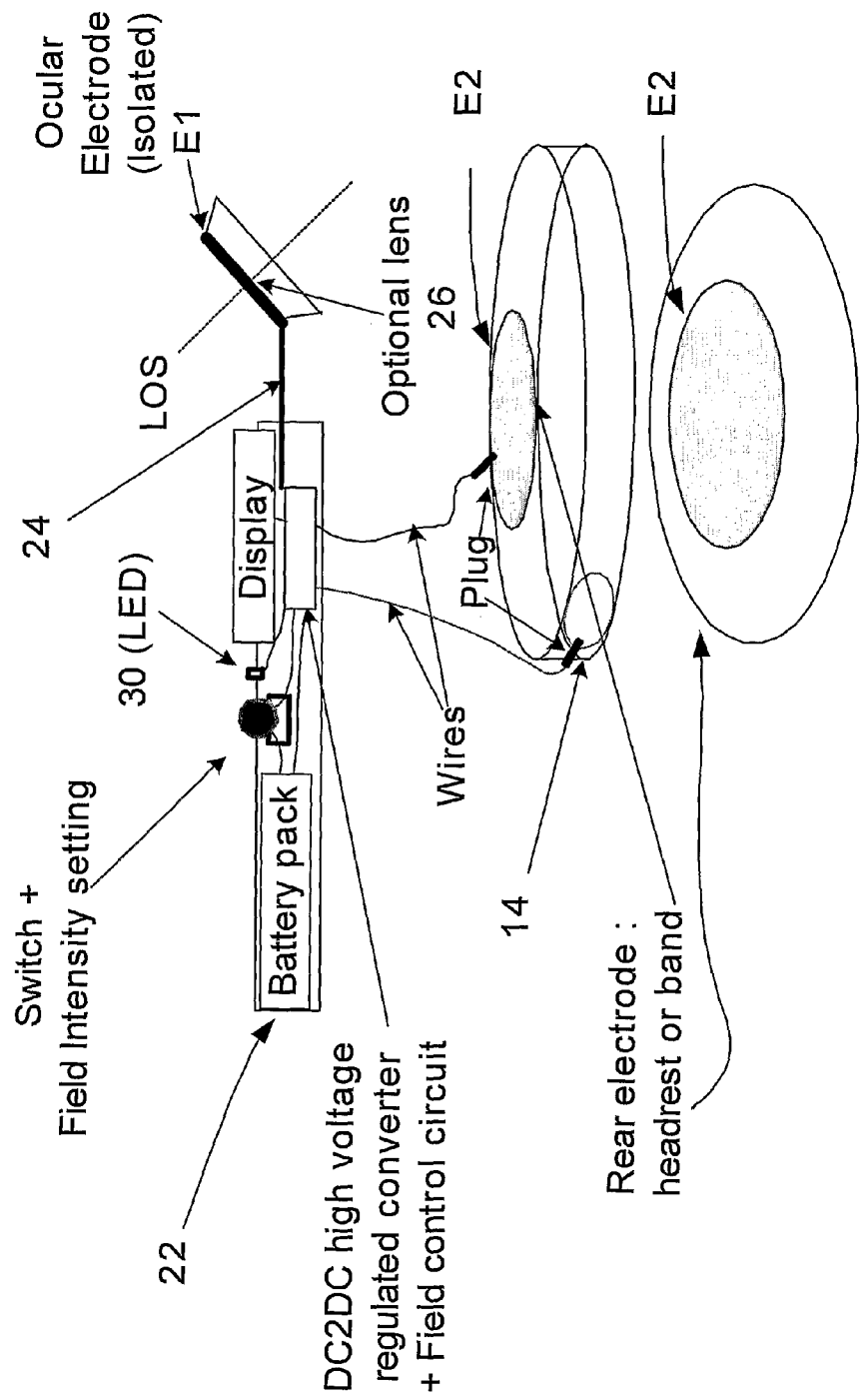

Reference is made to FIGS. 2A-2C showing a specific but not limiting example of the implementation of the present invention. As shown in FIG. 2A, a device 100 includes an external field source 12 (electric field source in the present example), a field sensor 14, and a control unit 16. The electric field source 12 includes an electrode arrangement 12A and a voltage supply unit 12B. The electrode arrangement 12A includes an annular ocular electrode $E_1$ connected to voltage supply unit 12B via a conductor grip 15, and a second complementary electrode $E_2$ to be attached to a seat headrest or a head-band. A lens may be located within the hole of the ocular electrode $E_1$. The electrodes $E_1$ and $E_2$ are electrically connected to the voltage supply unit 12B (DC2DC circuit) to be supplied with different voltages defining a desired potential difference between them. The control unit 16 is interconnected (via wires or wireless) between voltage supply unit 12B and field sensor 14. Voltage supply unit 12B and control unit 16 are connected to a power source (battery pack) 20.

As shown in FIG. 2B, the device has a hand held probe 22 containing the voltage supply unit and preferably the control unit (which are not shown here) with a display 16C being exposed to user, and the annular-shaped ocular electrode $E_1$ is located outside the probe 22 being connected to the voltage supply unit via an insulated wire connector 24 (preferably sufficiently flexible connector). A lens 26 is optionally provided in the ocular electrode hole, such that the electrode $E_1$ serves as the lens carrier. The electrode $E_1$ may be optically transparent. The device 100 allows a hand held free operation as is performed by physicians when examining the retina. The second electrode $E_2$ is located as described above and a voltage supply thereto may or may not be controlled (e.g., the device operation can be controlled only by controlling the voltage supply to the ocular electrode $E_1$).

Alternatively, the use of a second electrode $E_2$ can be replaced by a direct electrical contact with the patient's head or body, thus using it as the complementary end of the electrical field. If such an option is applied, it is also advised that this electrode is grounded, in order to prevent electrocution hazard.

As shown in FIG. 2C, in the present example, the field sensor 14 is mounted on the complementary electrode $E_2$. The lens 26 (the provision of which is optional) is inserted into the hole of electrically insulated ocular electrode $E_1$. The electrodes $E_1$ and $E_2$ are connected (by wires) to the voltage supply unit (DC2DC high voltage converter) located inside the housing 22. The field sensor 14 is connected (by wires or wireless) to the field control and field intensity setting circuit of the control unit located inside the housing 22. Considering the indirect opthalmoscope configuration of the device, the probe 22 to be held by a physician also carries a light source 30 (e.g., LED).

Reference is made to FIGS. 3 and 4A-4C exemplifying a device 200 of the present invention utilizing application of a magnetic field to the patient's eye. In the case of a magnetic field application, the magnetic field source can include a permanent magnet or coils or any form of a magnetic field generator. Furthermore, both the electric and magnetic fields may be applied.

Figure 3:
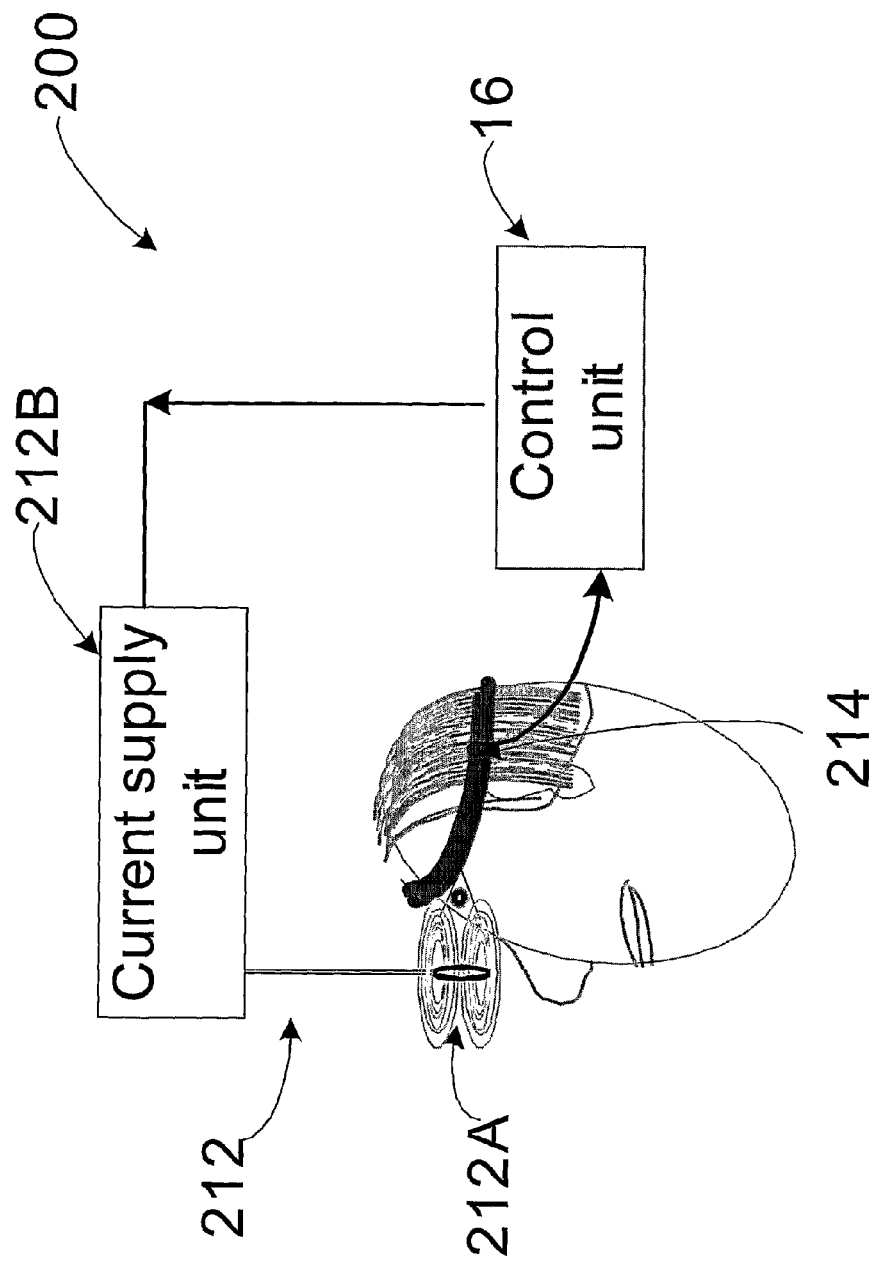
FIG. 3 is a schematic illustration of another example of a device of the present invention, utilizing a magnetic field source.

The device 200 includes a magnetic field source 212 formed by an electro-magnet unit (e.g., coil unit) 212A and a power supply unit (current supply unit) 212B. A control unit 16 is connected to the current supply unit 212B and to a magnetic field sensor 214 appropriately configured and accommodated for measuring the actual field value in the region of interest. Field source 212 is configured and operable to create a DC external magnetic field of a required profile within a field region FR. The field profile defines a required field value within a patient's eye (iris) location L in the field region. By this, an effect of mydriasis of the iris is temporary induced. Magnetic field lines are shown in FIG. 3.

The control 16 is configured and operable to modify the applied current through the coil 212A according to the feedback obtained from the field sensor 214 and applied settings (instead of controlled voltage in the case of electric field application). In the case of a magnetic field application, a single coil unit may for example be used.

The coil unit 212A is accommodated in the vicinity of patient's eye such that the field lines B mostly pass through the iris location L. The coil unit 212A may be of an annular shape defining a hole large enough to enable visual inspection of the eye via the enlarged pupil. Such an ocular hole may be used for combining lenses commonly used by eye physicians for retina examination or indirect opthalmoscope, as described above. It should be understood that generally, the ocular element may be formed by one or more magnetic elements, one of them having an annular shape to allow eye examination therethrough.

The magnetic field profile within the field region FR and accordingly the field intensity at the iris location L within this region is defined mainly by a field intensity at the coil unit 212A and a distance from the iris. This magnetic field inhibits nervous impulses to iris muscles. It should be noted that the magnetic field polarity could be of either type.

Similar to the electric field case, in order to desirably affect the pupil size (e.g., achieve a mydriasis effect), a minimal magnetic field intensity level should be present at the iris location L. This field intensity depends mainly on the applied current through the coil, distance and attitude of the coil with respect to the iris, and magnetic characteristics of the specific patient. To this end, the device 200 utilizes a closed-loop control circuit. The latter is formed by the field sensor 214 located within the field region FR and configured and operable for measuring the actual field intensity value and generating data indicative thereof; the control unit 16 and the current supply unit 212B. The required field intensity at location L is set by user and controlled using a feedback signal of the control unit 16 based on data measured by the field sensor 214. The field sensor 214 may have any known suitable configuration, for example based on employing the magnetoresistive effect of thin-film perm-alloy. The current supply unit 212B is a high DC current source circuit generating the required currents to the coil unit.

Thus, in the case of magnetic field, the device of the present invention provides for affecting synaptic transmission to desirable modulate the pupil size by inhibiting neurotransmitters arrival to receptors by diverting them from their course using an orthogonal field.

Figure 4A:
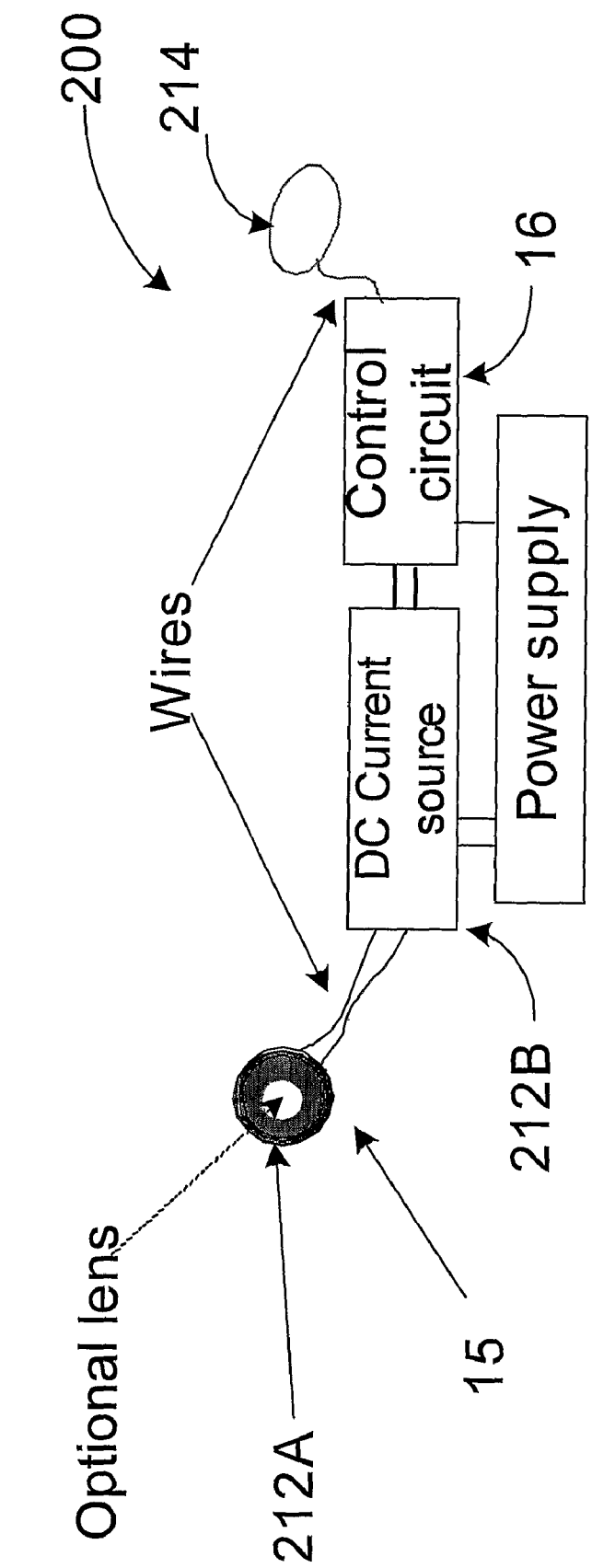
FIGS. 4A to 4C exemplify the specific implementation of the device of FIG. 3.
Figure 4B:
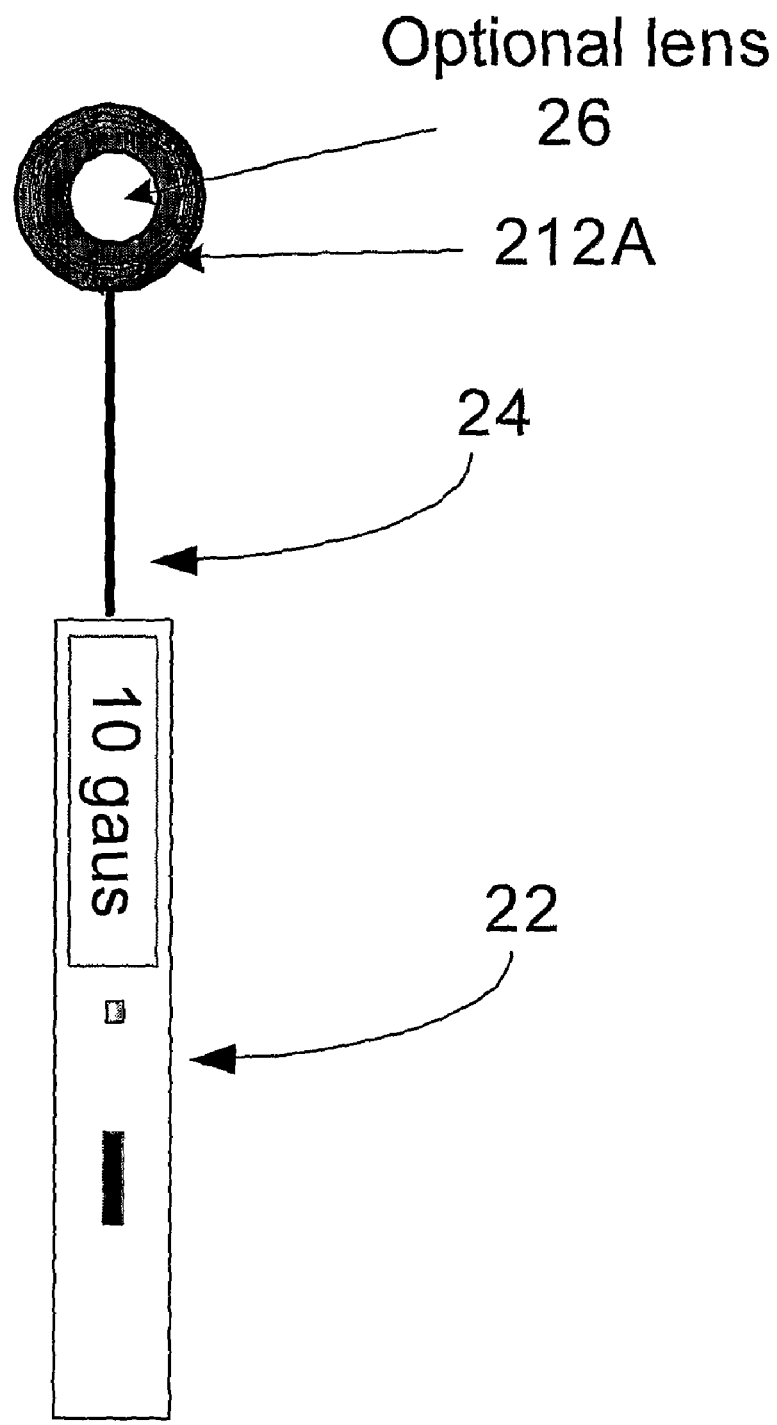
Figure 4C:
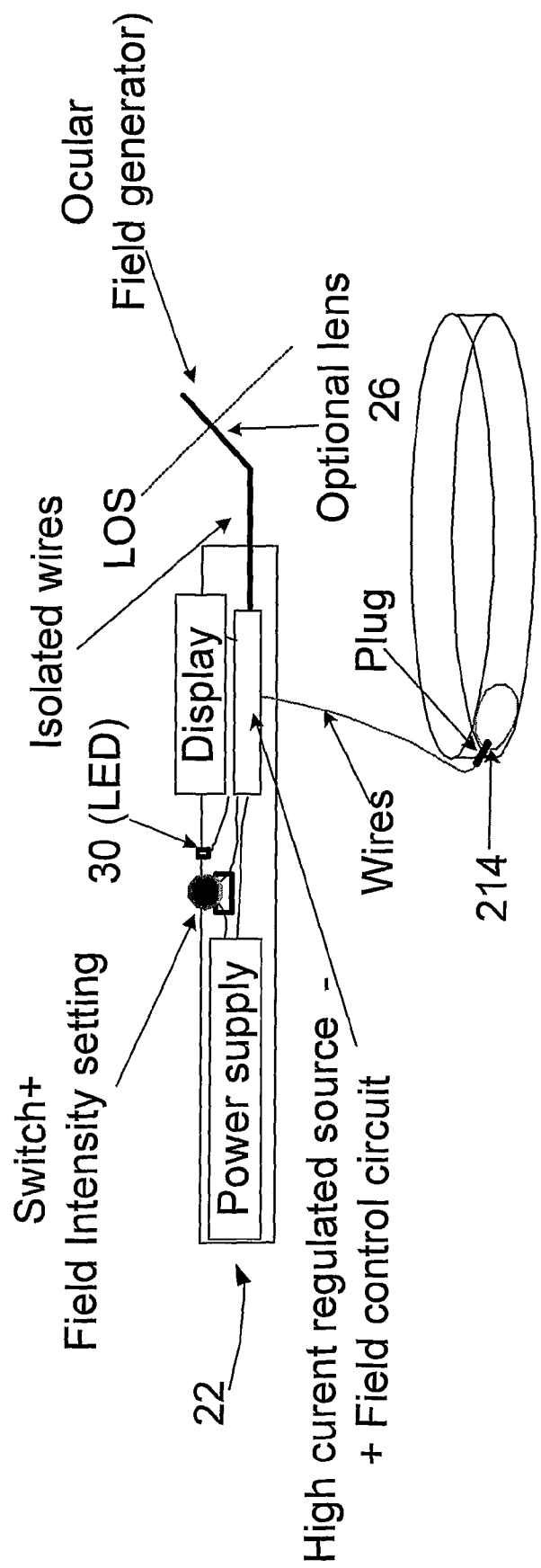

FIGS. 4A-4C show a specific, but not limiting, example of the implementation of the device of FIG. 3. As shown in FIG. 4A, the device 200 includes an external magnetic field source 212, a magnetic field sensor 214, and a control unit 16. The magnetic field source 212 includes a coil unit 212A and a current supply unit 212B. The coil unit 212A includes an annular ocular coil connected to current supply unit 212B (controllable DC current source) via a conductor grip 15, to be therefore supplied with different currents defining a desired magnetic field intensity in the region of interest. A lens may be located within the hole of the ocular coil. The control unit 16 is interconnected (via wires or wireless) between the current supply unit 212B and field sensor 214. Current supply unit 212B and control unit 16 are connected to a power source 20.

As shown in FIG. 4B, the device has a hand held probe 22 containing the current supply unit and the control unit (which are not shown here) with a display 16C being exposed to user, and the annular-shaped ocular coil 212A is located outside the probe 22 being connected to the current supply unit via an insulated wire connector 24 (preferably sufficiently flexible connector). A lens 26 is optionally provided in the ocular coil hole, such that the coil serves as the lens carrier. The coil may be optically transparent. The device 200 allows a hand held free operation as is performed by physicians when examining the retina.

As shown in FIG. 4C, in the present example, the field sensor 214 is mounted on the head band. The lens 26 (the provision of which is optional) is inserted into the hole of electrically insulated ocular coil 212A. The latter is connected (by wires) to the current supply unit located inside the housing 22. The field sensor 214 is connected (by wires or wireless) to the field control and field intensity setting circuit of the control unit located inside the housing 22. Considering the indirect opthalmoscope configuration of the device, the probe 22 to be held by a physician also carries a light source 30 (e.g., LED).

Figure 5:
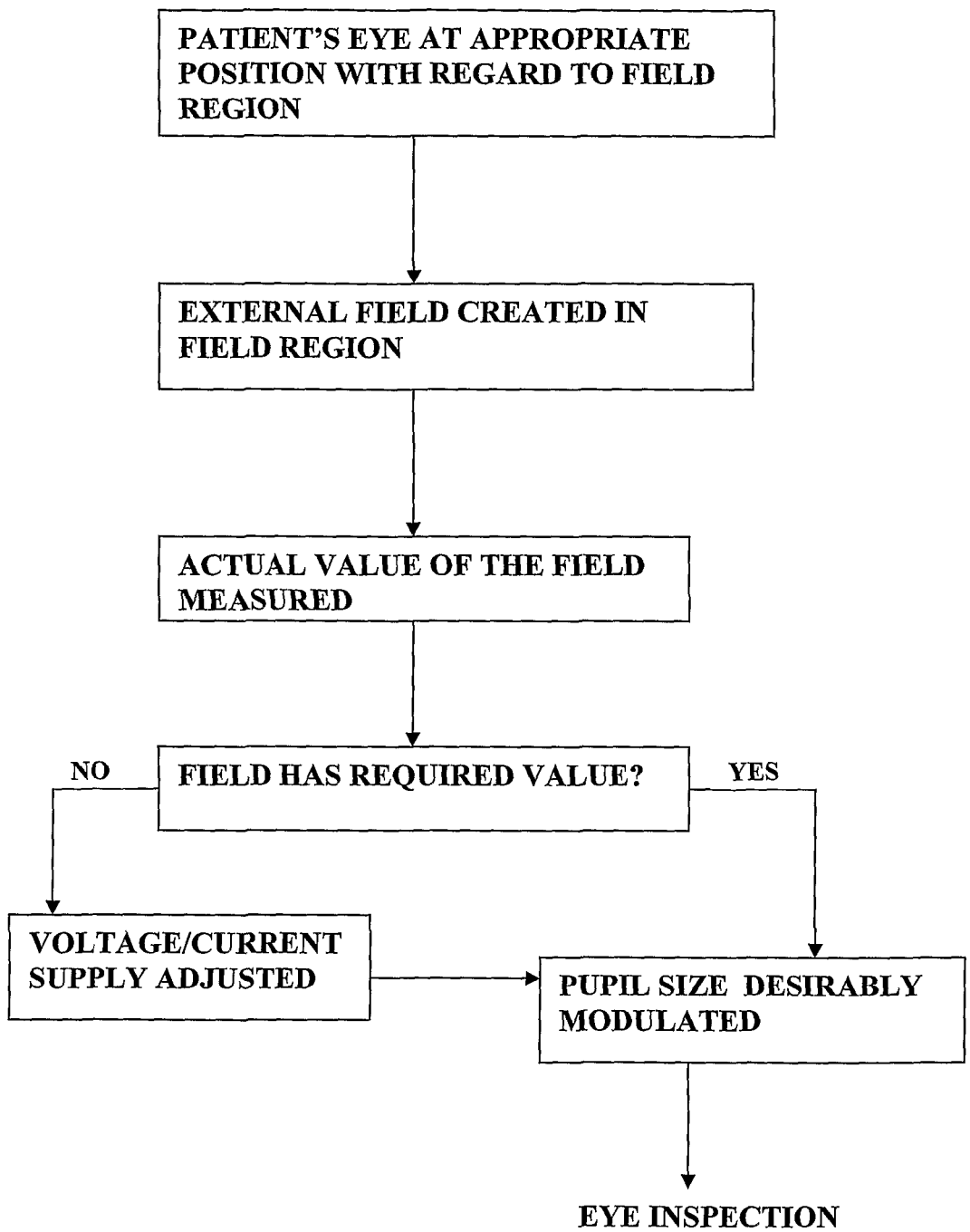
FIG. 5 is a flow diagram of a method of the present invention.

FIG. 5 shows the flow diagram of a method of the present invention. The patient is positioned such that his eye is at a desired location within an expected field region. The external field (electric and/or magnetic) is created in this region (by bringing the ocular element, electrode and/or coil, close to the patient's eye, and in the case of electric field possibly also appropriately arranging the rear complementary electrode). The control unit operates the field source to measure the actual field value in the vicinity of the patient's eye, and if needed operates the voltage and/or current supply unit to readjust the field intensity, thereby causing the pupil size modulation and allowing eye inspection via the enlarged pupil.

The following are the results of experiments conducted by the inventors. In these experiments, the electric field application was used.

Table I presents the experimental data for the first set of experiments. An experimental set up used in these experiments included a disk-shaped ocular electrode and a field generating DC voltage of 99.8V. Two methods were used: proximity of the active ocular electrode to the iris; and ON/OFF power application whereas no effects are eminent when power is OFF, and the pupil reacts to illumination changes as usual. Direct illumination of the examined eye was applied in both cases; turning the illumination ON and OFF during the device operation did not affect the pupil size. The results were in the form of a pupil diameter, and were obtained using standard ophthalmic measurement equipment including magnifying lenses. Two parameters were controlled to estimate their effect on the measurements: voltage polarity (positive polarity being connected to the ocular electrode); and the complementary electrode position (head rest, or near the temple).

In these experiments, the actual distance between the ocular electrode and the eye was not fixed from one test to the other, and no feedback mechanism was used, thus the resulting effect varies due to the hand held proximity variance. It should be understood that the required field effect uniformity could be achieved by using the feedback and control mechanism. These experiments just demonstrate the actual pupil size modulation effect. Each test included precise measurements of the subject's pupil diameter, using standard ophthalmic measurement equipment with accuracy of 0.05 mm. Pupil diameter measurements were performed at the beginning of each test and under the operation of a device of the present invention (configured for the application of electric field), and showed an increase in pupil diameter accordingly. In these tests, a probe carrying an annular-shaped ocular electrode was brought to the patient's eye to position the ocular electrode to maximal proximity of the eye, without actual contact (in the vicinity of the eye lashes). A complementary electrode (the provision of which is optional) was configured as a plate (in an insulating cover) and located aside the patient's head. In order to perform a full retina inspection, a minimal pupil diameter of 4 mm is required, which was achieved in the experiments. Furthermore, voltage level can be increased to cater for a stronger pupil size modulation effect and a larger position space of the ocular electrode. Tested variants included lighting intensity (upon which initial pupil diameter reacted); complementary electrode connection; one idle operation (no voltage applied). Test results where recorded on both video and photographs. The tests were performed using 99.8 DCV applied between the ocular electrode and the complementary electrode, where the ocular electrode was connected to the negative pole. The ocular electrode consisted of a conductive washer-like ring, coated with isolative material and was carried by an isolated handle. Each test included two measurements: initial measurement (with no electric field application) and measurement upon applying the electric field.

TABLE I

| Test | Light intensity level | Complementary electrode position/connection | Voltage | Initial pupil diameter | Modulated pupil diameter | Record type |
|---|---|---|---|---|---|---|
| 1 | 1 | Isolated near temple | 99.8 VDC | 2.7 mm | 3.5 mm | Photo |
| 2 | 2 | Isolated near temple | 99.8 VDC | 2.3 mm | 4.1 mm | Photo |
| 3 | 1 | Isolated near temple | 99.8 VDC | 2.5 mm | 3.9 mm | Video |
| 4 | 1 | Isolated near temple | 0 VDC | 2.6 mm | 2.6 mm | Video |
| 5 | 1 | Positive pole conductive, connected to subject's chin & earthed | 99.8 VDC | 2.6 mm | 3.4 mm | Video |

Table II presents further experimental data obtained with the device configuration for the electric field application to the patient's eye. The device included a round, washer-like plate-like ocular electrode. The latter was placed at a 5 mm distance to the patient's eye. The second, complementary electrode was in the form of a rectangular plate located near temple. The experiments were carried out under room dimmed light with different voltage values (i.e. a potential difference between the two electrodes):

TABLE II

| Test | Illumination | Voltage | $L_{ref}$ | $L_{mea}$ | Modulated pupil diameter |
|------|--------------|---------|-----------|-----------|--------------------------|
| 1 | Room dimmed light | 30 V | 22.34 | 20.396 | 4.6 |
| 2 | Room dimmed light | 40 V | 22.34 | 20.396 | 4.6 |
| 3 | Room dimmed light | 50 V | 22.34 | 20.03 | 4.5 |

In these experiments, the measurement method includes analysis of photographs, taken of the examined eye, and calculation of the pupil size according to the ratio between the $L_{mea}$ (measured pupil diameter from the picture) and $L_{ref}$ (a scale of 5 mm notches, photographed in the measurement picture).

Table III shows yet further experimental data obtained with the ocular electrode of an ice cream scrapper shape and the complementary electrode in the form of a side plate near the temple, under room light. In this Table, tests 1-3 and 4 correspond to tests carried out on two different patients, respectively: test 1 data corresponds to the initial state of the patient's eye, i.e. with no application of external field; tests 2 and 3 data correspond to said eye under the application of an electric field by applying different voltages (potential difference between the electrodes), and test 4 data corresponds to the experimental results for the second patient. In these experiments, a ratio between the pupil and iris is calculated (whereas the iris size does not change and serves as a constant reference).

TABLE III

| Test | Illumination | Voltage | Iris/pupil ratio | Expansion ratio | Estimated pupil size |
|------|--------------|---------|------------------|-----------------|----------------------|
| 1 | Room light | Not applied | 71/22.3 = 3.18 | | 9/3.18 = 2.8 mm |
| 2 | Room light | 60 V | 72/31.9 = 2.26 | 3.18/2.26 = 1.4 | 9/2.36 = 4 mm |
| 3 | Room light | 70 V | 60.6/29.5 = 2.05 | 3.18/2.05 = 1.55 | 9/2.05 = 4.4 mm |
| 4 | Room light | 70 V | 53.5/24.0 = 2.23 | 3.18/2.23 = 1.52 | 9/2.23 = 4.1 mm |

Thus, the present invention provides a simple and effective, drug-free temporary modulation of a pupil size (dilation/contraction of the pupil), by effecting stimulation or neutralization of the synapses by subjecting the iris to an external electric and/or magnetic field of desired properties (direction and intensity)

Those skilled in the art to which the present invention pertains can appreciate that while the present invention has been described in terms of preferred embodiments, the concept upon which this disclosure is based may readily be utilized as a basis for the designing of other structures, systems and processes for carrying out the several purposes of the present invention.

Also, it is to be understood that the phraseology and terminology employed herein are for the purpose of description and should not be regarded as limiting.

It is important, therefore, that the scope of the invention is not construed as being limited by the illustrative embodiments set forth herein. Other variations are possible within the scope of the present invention as defined in the appended claims and their equivalents.

The invention claimed is:

1. A device for modulation of a pupil size, wherein:
   the device is configured for drug-free non-invasive modulation of a pupil size without actual contact with a patient's eye,
   the device consists of one or more units for placing externally to a patient's eye without actual contact with a patient's eye, and
   the device comprises an external source of an electric and/or magnetic field for placing externally to a patient's eye, said external source of the electric and/or magnetic field being configured and operable to produce the electric and/or magnetic field of desired intensity and direction having a required profile of the field in a region at a certain distance from the external source, such that temporal application of said field to an iris region in the patient's eye effects stimulation and/or neutralization of a nervous impulse to iris muscles associated with the pupil control, thus temporarily inducing mydriasis or miosis effect, the device thereby providing drug-free non-invasive modulation of a pupil size.

2. The device of claim 1, comprising an external sensor for locating in the vicinity of the field region, the sensor being configured for measuring intensity of the actual electric and/or magnetic field, as produced by the external field source, in the vicinity of the sensor and generating data indicative thereof; and a control unit configured to be responsive to the data indicative of the measured field intensity, to process and analyze said data and upon detecting that adjustment of the field intensity is required generate a control signal for operating the external field source.

3. The device of claim 2, wherein the field sensor is attached to a head band to be put on the patient's head.

4. The device of claim 1, wherein the external field source comprises an ocular element configured to be brought close to the patient's eye and having an electrically insulated surface by which it faces the patient's eye.

5. The device of claim 4, wherein the external field source is configured for generating the magnetic field, said ocular element being an electro-magnet unit and being connected to a current supply unit.

6. The device of claim 5, wherein the electro-magnet unit has an annular shape to enable inspection of the eye via a hole of the ocular electro-magnet unit.

7. The device of claim 6, wherein said annular-shaped electro-magnet unit is configured for mounting a lens in said hole.

8. The device of claim 5, comprising a hand held or stationary housing containing the current supply unit and the control unit, the ocular electro-magnet unit being located outside said housing and being connected to the current supply unit by an electrically insulated connector.

9. The device of claim 8, wherein the control unit comprises a display located at the outer surface of the housing to be exposed to user.

10. The device of claim 4, wherein the electro-magnet unit includes one or more magnetic element, at least one said magnetic element being shaped so as to allow visual eye inspection therethrough.

11. The device of claim 1, wherein the external electric field source comprises an electrode arrangement, and a voltage supply unit.

12. The device of claim 11, wherein the electrode comprises a first ocular electrode, a direct electric contact to the patient's body serving as a second complementary electrode.

13. The device of claim 11, wherein the first ocular electrode is configured to be brought close to the patient's eye, and has an electrically insulated surface by which it is brought to the patient's eye without contacting it.

14. The device of claim 11, wherein the first ocular electrode has an annular shape to enable inspection of the eye via a hole of the ocular electrode.

15. The device of claim 14, wherein said first annular-shaped electrode is configured for mounting a lens in said hole.

16. The device of claim 11, comprising a hand held or stationary housing containing the voltage supply unit and the control unit, a first ocular electrode of the electrode arrangement being located outside said housing and being connected to the voltage supply unit by an electrically insulated connector.

17. The device of claim 16, wherein the control unit comprises a display located at the outer surface of the housing to be exposed to user.

18. The device of claim 1, wherein the external electric field source comprises an electrode arrangement formed by first and second electrodes located in a spaced-apart relationship defining the electric field region between them, and a voltage supply unit operable to provide a certain potential difference between the electrodes.

19. The device of claim 18, wherein the second complementary electrode is configured to be attached either to the patient's head or to a seat headrest.

20. The device of claim 19, wherein the sensor is attached to said head band.

21. The device of claim 18, wherein the second complementary electrode is configured for connecting it directly to the patient's body.

22. The device of claim 18, wherein the second complementary electrode is configured to be isolated or non-isolated.

23. The device of claim 18, wherein the second complementary electrode is carried by a head band to be put on the patient's head.

24. The device of claim 18, wherein each of the first and second electrodes includes one or more electrode elements of respective polarity.

25. The device for use in dilation/contraction of a patient's pupil, wherein:
the device is configured for drug-free non-invasive modulation of a pupil size without actual contact with a patient's eye,
the device consists of one or more units for placing externally to a patient's eye without actual contact with a patient's eye, and
the device comprises:
an external source of an electric and/or magnetic field for placing externally to a patient's eye, said external source of the electric and/or magnetic field being configured and operable to define a field region at a certain distance from said source, and to produce electric and/or magnetic field of desired intensity and direction defining a desired field profile in said field region, such that said field profile when applied to a patient's eye is located within said region temporarily induces an effect of mydriasis or miosis via stimulation or neutralization of a nervous impulse to iris muscles;
an external sensor located in the vicinity of said field region and configured for measuring the intensity of the actual field in the vicinity of the sensor and generating data indicative thereof; and
a control unit configured to be responsive to the data indicative of the measured field intensity to process and analyze said data and upon detecting that adjustment of the field value is required generate a control signal to the external field source.

26. A device for use in dilation/contraction of a patient's pupil, wherein:
the device consists of one or more units for placing externally to a patient's eye without actual contact with a patient's eye, the device comprising:
a hand-held housing containing a current supply unit operable to apply current to an electro-magnet unit located outside said housing and connected to the current supply unit via a connector extending from the housing to said electro-magnet unit, the electro-magnet unit having a substantially annular shape so as to enable visual observation of the eye via an opening defined by the annular-shaped electro-magnet unit, the electro-magnet unit being configured and operable such that the device, while without actual contact with the patient's eye, generates a magnetic field of a desired direction and intensity creating a desired field profile within a field region at a certain distance from the electro-magnet unit where a patient's eye is to be located when the device is put in operation while being held at a distance from the patient's eye, said intensity and direction of the field being controlled to temporarily induce an effect of mydriasis or miosis via stimulation or neutralization of a nervous impulse to iris muscles, the electro-magnet unit.

* * * * *